United States Patent [19]

Ogawa et al.

[11] Patent Number: 4,730,058
[45] Date of Patent: Mar. 8, 1988

[54] SIALOSYLCERAMIDES AND PRODUCTION METHOD THEREOF

[75] Inventors: Tomoya Ogawa, Tokyo; Mamoru Sugimoto; Masaaki Numata, both of Saitama; Yoshiyasu Shitori; Masayoshi Ito, both of Tokyo, all of Japan

[73] Assignee: Mect Corporation, Tokyo, Japan

[21] Appl. No.: 36,445

[22] Filed: Apr. 9, 1987

[30] Foreign Application Priority Data

Apr. 11, 1986 [JP] Japan .................................. 61-83396

[51] Int. Cl.$^4$ .................. C07D 309/00; C07D 309/02
[52] U.S. Cl. .................................... 549/214; 549/416; 549/417; 549/419
[58] Field of Search ................ 549/214, 416, 417, 419

[56] References Cited

U.S. PATENT DOCUMENTS 3,939,043  2/1976  Nara et al. ....................... 549/419 X
4,120,824 10/1978  Crutchfield et al. ............ 549/419 X

FOREIGN PATENT DOCUMENTS 146810    3/1985  European Pat. Off. ............ 549/214
59-164798 9/1984  Japan ............................... 549/214 X

OTHER PUBLICATIONS

Carbohydrate Research, vol. 128, 1984, pp. C1–C4, Elsevier Science Publishers B.V., Amsterdam, NL; T. Ogawa et al: "Synthesis of Alpha– and Beta–(2-9-)–Linked Disialyglycerolipids", European Search Report 87 10 5321.

Primary Examiner—Paul F. Shaver
Attorney, Agent, or Firm—Oblon, Fisher, Spivak, McClelland & Maier

[57] ABSTRACT

This invention provides a novel compound expressed by the following formula (1):

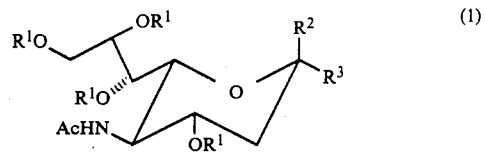

(1)

[wherein $R^1$ denotes a hydrogen atom or $CH_3CO-$, $R^2$ denotes $-COOR^4$ ($R^4$ denotes Na or a methyl group) or

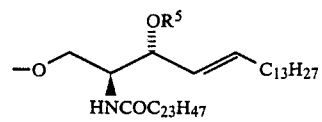

($R^5$ denotes a hydrogen atom, $-COC_6H_5$ or $-Si(C_6H_5)_2C(CH_3)_3$ and $R^3$ denotes

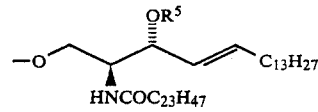

($R^5$ denotes a hydrogen atom, $-COC_6H_5$ or $-Si(C_6H_5)_2C(CH_3)_3$) when $R^2$ is $-COOR^4$ ($R^4$ denotes Na or a methyl group) or denotes $-COOR^4$ when $R^2$ is

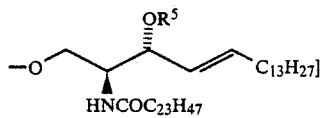

and a method of preparation thereof.

The above novel compounds of present invention are useful as a tumor maker, a molecular marker for cells having the ability of differential induction, or an intermediate of the synthesis thereof. 'Y 14 Claims, No Drawings

SIALOSYLCERAMIDES AND PRODUCTION METHOD THEREOF

BACKGROUND OF THE INVENTION

The present invention relates to novel sialosylceramides and a production method thereof.

The glycolipid of mammalian cells comprises a lipid structure expressed as a ceramide in which a fatty acid is amido-bonded to sphinogosine of a long chain amino alcohol and to which sugars such as glucose, galactose, N-acetylglucosamine, N-acethylgalactosamine, fucose, and sialic acid are bonded through glicosidic linkage in various combinations, and belongs to the category of so-called sphingoglycolipids. In particular, the glycolipid having sialic acid is called ganglioside.

Most of these compounds are generally located in the outer molecular layer of the two molecular layers of cell membrane and it has been thought from recent investigations that the compounds play an important role in the function as a reception and response receptor of recognition and information, differentiation, proliferation, malignant change, or behavior in cells.

However, the function of ganglioside-based glycolipid as a component of cell membrane has not been sufficiently elucidated and it is difficult to isolate ganglioside from an organism and purify it.

Although precision synthesis of $GM_3$ (GM: ganglioside monosialo) and $GM_4$ has been successfully achieved, the synthesis of an unnatural compound ($GM_5$) of the present invention which has a similar structure to that of the above compounds is necessary and indispensable to the elucidation of the function of the ganglioside-based glycolipid as a component of cell membrane.

SUMMARY OF THE INVENTION

An object of the present invention is to provide novel sialosylceramides and a production method thereof.

The present invention relates to a compound expressed by the following formula (1):

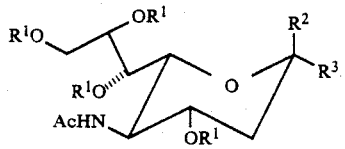
(1)

[wherein $R^1$ denotes a hydrogen atom or a $CH_3CO$ group, $R^2$ denotes $-COOR^4$ ($R^4$ denotes Na or a methyl group) or

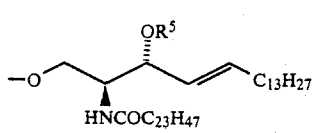

($R^5$ denotes a hydrogen atom, $-COC_6H_5$ or $-Si(C_6H_5)_2C(CH_3)_3$), and $R^3$ denotes

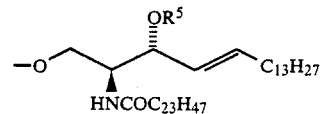

($R^5$ denotes a hydrogen atom, $-COC_6H_5$ or $-Si(C_6H_5)_2C(CH_3)_3$) when $R^2$ is $-COOR^4$ or denotes $-COOR^4$ when $R^2$ is

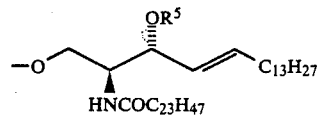

($R^4$ denotes Na or a methyl group)]
and a production method thereof.

Typical examples of the compound expressed by the formula (1) of the present invention are indicated below.

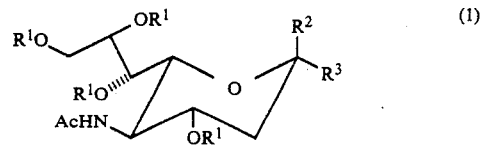

Compound (I):

$R^1 = CH_3CO,$

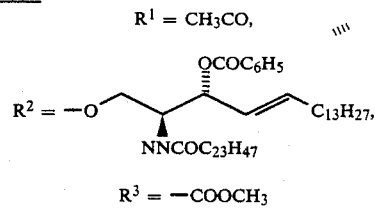

$R^3 = -COOCH_3$

Compound (II):

$R^1 = CH_3CO, R^2 = -COOCH_3,$

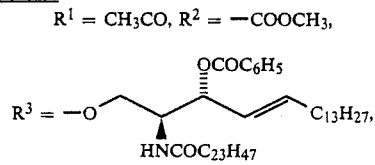

Compound (III):

$R^1 = H,$

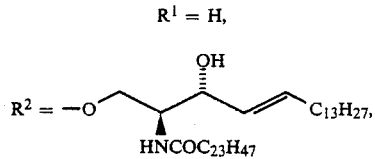

$R^3 = -COONa$

Compound (IV):

$R^1 = H, R^2 = -COONa,$

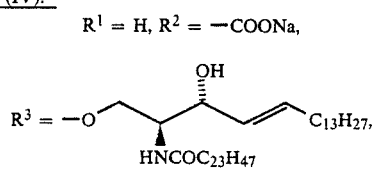

Compound (VII):

$R^1 = CH_3CO,$

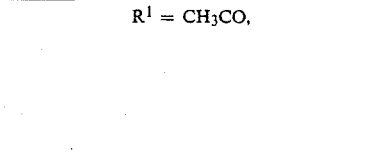

-continued $R^2 = $ 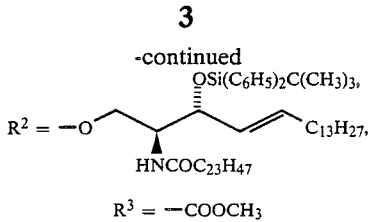

$R^3 = -COOCH_3$

Compound (VIII):

$R^1 = CH_3CO, R^2 = -COOCH_3,$ $R^3 = $ 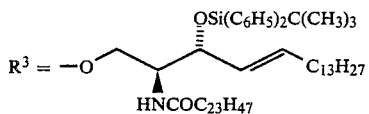

A production method of the present invention will be described in detail below with reference to schemes I to III.

The compound (V) is prepared from N-acetyl-neuraminic acid methyl ester peracetate by the method of Kuhn and others (refer to Chem. Ber., 99, 611–617 (1966)).

The compound (VI) which is a ceramide portion is produced by the method disclosed in Japanese Patent Application No. 44913/1984 [Japanese Patent Disclosure No. 190745/1985].

The compound (IX) which is also a ceramide portion is produced by the method disclosed in Japanese Patent Disclosure No 190745/1985 or Japanese Patent Application No. 248981/1986 (See scheme III).

The compound (VI) or (IX), a glycosidation catalyst such as silver trifurate, a solvent such as dichloroethane, a mixed solution of tetrahydrofuran and chloroform, nitromethane, tetrahydrofuran or chloroform are added to M.S. (molecular sieves) 4A or AW300, and the mixture is agitated at room temperature for about 1 to 6 hours. Then, a solution containing the compound (V), and a solvent such as dichloroethane, a mixed solution of tetrahydrofuran and chloroform, nitromethane, tetrahydrofuran or chloroform is added to the resulting mixture under cooling, for example, with ice-methanol, and agitated at room temperature for about 10 to 20 hours after being allowed to stand for about 0.5 to 2 hours. The reaction solution is filtered and chloroform is added to the filtrate which is then washed with a saturated aqueous solution of sodium hydrogen carbonate and saturated salt water, dried with anhydrous magnesium sulfate, and subjected to vacuum distillation. The residue is purified by a known means such as a silica gel column to obtain the compounds (I) and (II) or compounds (VII) and (VIII).

The compound (I) is dissolved in methanol and sodium methoxide is added to the methanol solution and agitated at room temperature for about 3 to 12 hours. After the reaction has been completed, the reaction solution is subjected to vacuum distillation and methanol, tetrahydrofuran, and distilled water are added to the residue and agitated at room temperature for about 10 to 20 hours. The reaction solution is neutralized with IRC-50, filtered, and then subjected to vacuum distillation. The residue is purified by a known means such as a Sephadex LH-20 column to obtain the compound (III).

The compound (III) can be obtained by treating the compound (VII) in the same manner as the above.

The compound (IV) can be obtained by treating the compound (II) or (VIII) in the same manner as the above.

SCHEME I
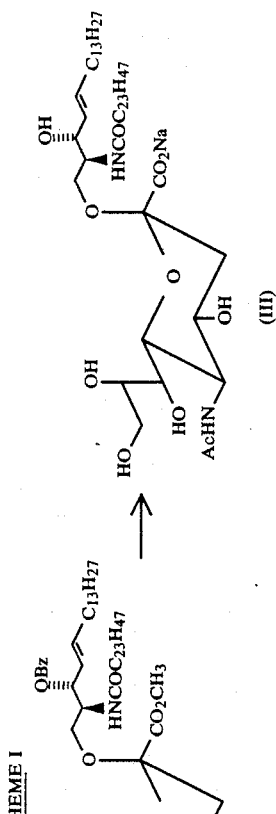
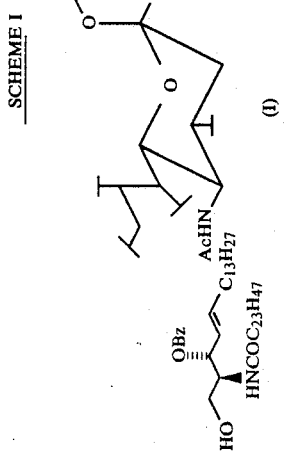
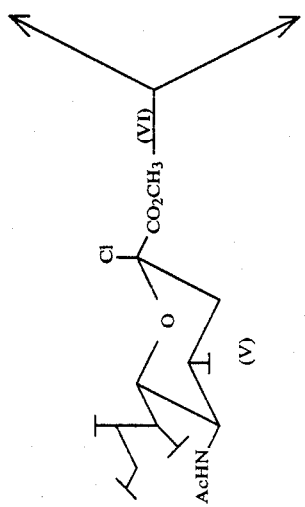
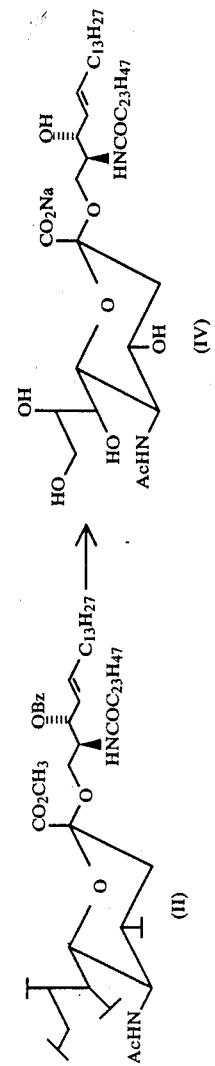

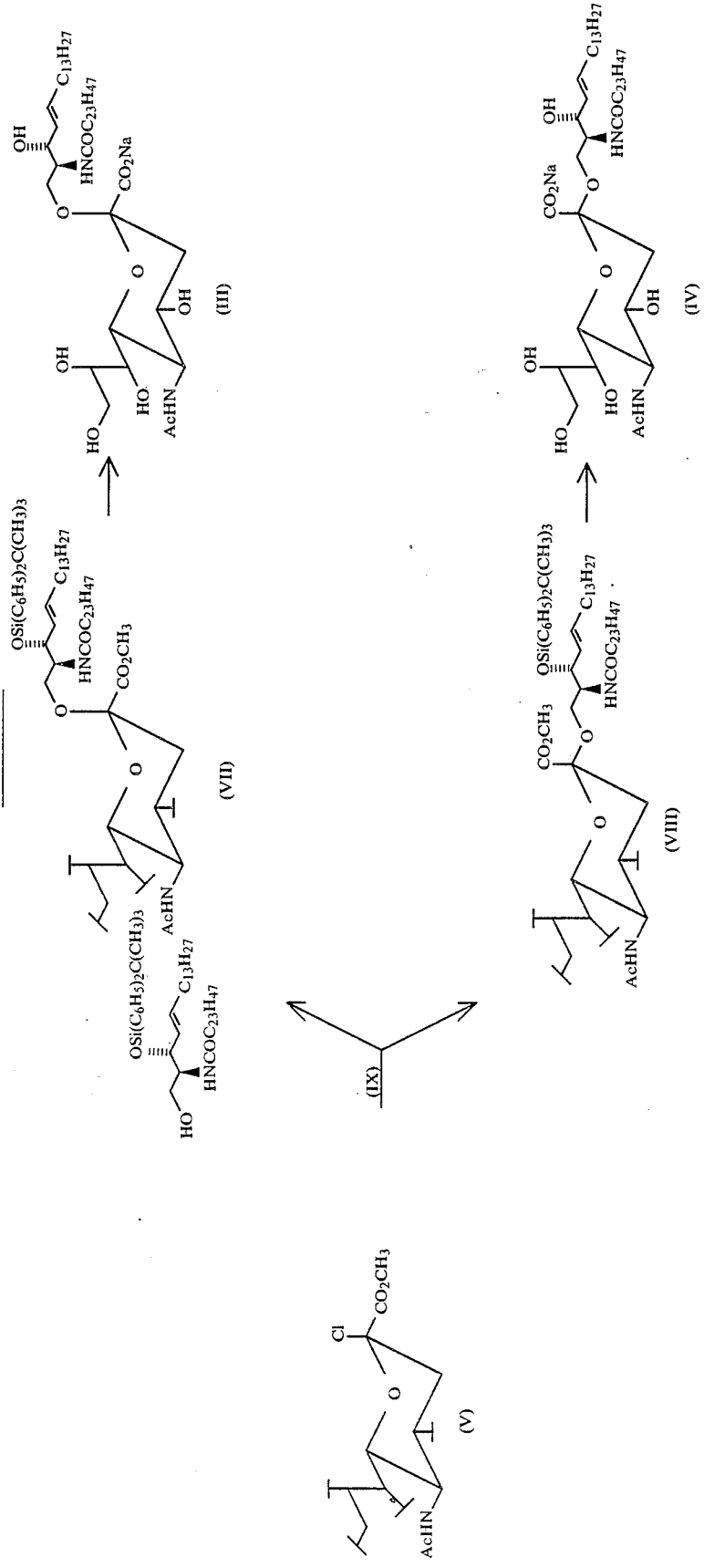

Scheme III

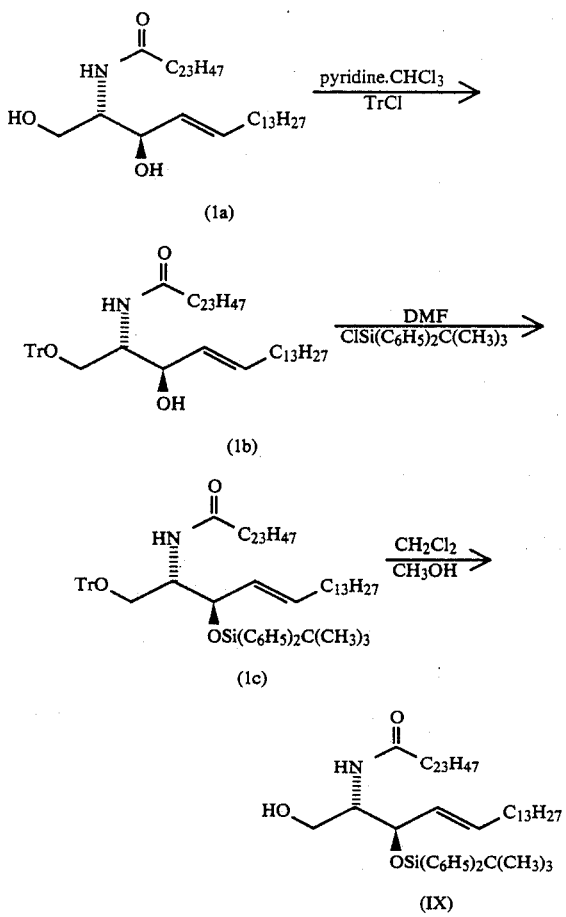

All the compounds (I), (II), (III), (IV), (VII) and (VIII) which are synthesized by the above-mentioned scheme are novel compounds.

Usefulness

The above novel compounds of the present invention are useful as a tumor maker, a molecular marker for cells having the ability of differential induction, or an intermediate of the synthesis thereof.

EXAMPLES

The present invention is described in detail below with reference to examples.

EXAMPLE 1

100 mg (0.13 milimol) of the compound (VI), 400 mg (1.5 milimol) of silver triflate, 3 ml of dichloroethane were added to 1 g of activated molecular sieves 4A and stirred at room temperature for 3 hours under argon atmosphere. Then, 1 ml of dichloroethane solution containing 50 mg (0.1 milimol) of the compound (V) was added to the resulting solution under cooling with ice-methanol bath and stirred at room temperature for 15 hours after being allowed to stand for 1 hour. The resulting reaction solution was filtered and chloroform was added to the filtrate which was then washed with a saturated aqueous solution of sodium hydrogencarbonate and saturated sodium chloride water, dried over anhydrous magnesium sulfate, and concentrated under vacuum. The residue was purified by a silica gel column (Wako gel C-300, 25 g, toluene:ethyl acetate=1:2, chloroform:methanol=10:1) to obtain 17 mg (14%) of the compound (I) and 7 mg (6%) of the compound (II).

(Physical property of the compound (I))

Rf=0.30 (toluene:ethyl acetate=1:2)

$[\alpha]_D^{20}$ −1.33 (C=0.75, chloroform)

Elementary analysis: Calculated: C, 69.16; H, 9.32; N, 2.12; (+$C_6H_5CH_3$). Measured: C, 68.69; H, 9.73; N, 2.25.

$^1$H-NMR(CDCl$_3$): δH 3.772 (s, 3H, OMe), 2.107, 2.024, 1.961, 1.881, 1.885 (Ac×5), 0.879 (t, 6H, CH$_2$CH$_3$×2)

(Physical property of the compound (II))

Rf=0.29 (toluene:ethyl acetate=1:2)

$[\alpha]_D^{20}$ −2.40 (C=0.25, chloroform)

Elementary analysis: Calculated: C, 69.16; H, 9.32; N, 2.12; (+$C_6H_5CH_3$). Found: C, 69.22; H, 9.87; N, 2.18.

$^1$H-NMR(CDCl$_3$): δH 3.559 (s, 3H, OMe), 2.068, 2.033, 2.027, 2.023, 1.880 (Ac×5), 0.879 (t, 6H, CH$_2$CH$_3$×2)

EXAMPLE 2

100 mg (0.13 milimol) of the compound (VI), 400 mg (1.5 milimol) of silver triflate, 3 ml of a mixed solution of tetrahydrofuran and chloroform (1:1) were added to 1 g of molecular sieves 4A and stirred at room temperature for 3 hours under argon atmosphere. Then, 1 ml of a mixed solution of tetrahydrofuran and chloroform (1:1) containing 100 mg (0.2 milimol) of the compound (V) was added to the resulting solution under cooling with ice-methanol bath and agitated at room temperature for 15 hours after being allowed to stand for 1 hour. The obtained reaction solution was filtered and chloroform was added to the filtrate which was then washed with a saturated aqueous solution of sodium hydrogencarbonate and saturated sodium chloride water, dried over anhydrous magnesium sulfate, and concentrated under vacuum. The residue was purified by a silica gel column (Wako gel C-300, 25 g, toluene:ethyl acetate=1:2, chloroform:methanol=10:1) to obtain 70 mg (29%) of the compound (I) and 10 mg (42%) of the compound (II).

(Physical property of the compound (I))

Same as those of Example 1.

(Physical property of the compound (II))

Same as those of Example 1.

EXAMPLE 3

100 mg (0.13 milimol) of the compound (VI), 400 mg (1.5 milimol) of silver triflate, 3 ml of nitromethane were added to 1 g of molecular sieves AW300 and stirred at room temperature for 3 hours under argon atmosphere. Then, 1 ml of a nitromethane solution containing 100 mg (0.2 milimol) of the compound (V) was added to the resulting solution under cooling with ice-methanol bath and stirred at room temperature for 15 hours after being allowed to stand for 1 hour. The obtained reaction solution was filtered, the filrate was diluted with chloroform and then washed with a saturated aqueous solution of sodium hydrogencarbonate and saturated sodium chloride water, dried over anhydrous magnesium sulfate, and concentrated under vacuum. The residue was purified by a silica gel column (Wako gel C-300, 25 g, toluene:ethyl acetate=1:2, chloroform:methanol=10:1) to obtain 55 mg (23%) of the compound (I) and 60 mg (25%) of the compound (II).

(Physical property of the compound (I))

Same as those of Example 1.

(Physical property of the compound (II))

EXAMPLE 4

100 mg (0.13 milimol) of the compound (VI), 400 mg (1.5 milimol) of silver triflate, 3 ml of tetrahydrofuran were added to 1 g of molecular sieves AW300 and stirred at room temperature for 3 hours under argon atmosphere. Then, 1 ml of a tetrahydrofuran solution containing 100 mg (0.2 milimol) of the compound (V) was added to the resulting solution under cooling with ice-methanol bath and stirred at room temperature for 15 hours after being allowed to stand for 1 hour. The obtained reaction solution was filtered and chloroform was added to the filtrate which was then washed with a saturated aqueous solution of sodium hydrogencarbonate and saturated sodium chloride water, dried over anhydrous magnesium sulfate, and subjected to vacuum distillation. The residue was purified by a silica gel column (C-300, 25 g, toluene:ethyl acetate=1:2, chloroform:methanol=10:1) to obtain 70 mg (29%) of the compound (I) and 72 mg (30% of the compound (II).

(Physical property of the compound (I))
Same as those of Example 1.
(Physical property of the compound (II))
Same as those of Example 1.

EXAMPLE 5

14 mg (0.012 milimol) of the compound (I) was dissolved in 8 ml of methanol and 50 μl sodium methoxide was added to the obtained solution and stirred at room temperature for 6 hours. The reaction solution was subjected to vacuum distillation and 1 ml of methanol, 1 ml of tetrahydrofuran, and 0.5 ml of distilled water were added to the residue and stirred at room temperature for 15 hours. The reaction solution was neutralized with IRC-50, filtered, and then subjected to vacuum distillation. The residue was purified by a Sephadex LH-20 column (chloroform:methanol:water=60:30:4.6) to obtain 4.7 mg (43%) of the compound (III).

(Physical property of the compound (III))
Rf=0.63 (butanol:ethanol:water=2:1:1)
$^1$H-NMR δH (d$_6$ DMSO:D$_2$O=49:1, 30°); 1.858 (S, 3H, NHCO$\underline{CH_3}$); 0.853 (t, 6H, —CH$_2\underline{CH_3}$).
Decomposition point: 217°–222° C.

EXAMPLE 6

2.0 mg (50%) of the compound (IV) was obtained in the similar manner to that of Example 5 except that 30 μl of sodium methoxide was added to 5 mg (0.004 milimol) of the compound (II).

(Physical property of the compound (IV))
Rf=0.63 (butanol:ethanol:water=2:1:1)
$^1$H-NMR δH (d$_6$ DMSO:D$_2$O=49:1, 30°); 1.884 (S, 3H, NHCO$\underline{CH_3}$); 0.855 (t, 6H, —CH$_2\underline{CH_3}$).
Decomposition point: 74°–78° C.

EXAMPLE 7

According to the method described in Japanese Patent Application No. 248981/1986, the compound (IX) was prepared from the ceramide compound (1a).

The ceramide compound (1a) 1.360 g (2.09 m mol) was dissolved in pyridine 30 ml, and TrCl 722.8 mg (2.77 m mol) was added to the pyridine solution followed by stirring at 50° C. for 12 hours. Pyridine was removed from the reaction mixture and the residue was dissolved in chloroform. The chloroform solution was washed with water and saturated aqueous solution of sodium chloride, dried over anhydrous magnesium sulfate, and subjected to vacuum distillation. The residue was purified by a silica gel column (Wako gel C-300, 85 g, toluene:ethyl acetate=5:1 containing 2% Et$_3$N) to obtain 909 mg (45%) of the compound (1b).

DMF 15 ml, ClSi(C$_6$H$_5$)$_2$C(CH$_3$)$_3$ 370 mg (1.36 m mol) and imidazole 183 mg (2.69 m mol) were added to the compound (1b) 800 mg (0.90 m mol) followed by stirring at room temperature for 12 hours. Ether was added to the obtained reaction solution. The obtained ether solution was washed with water and a saturated aqueous solution of sodium chloride, dried over anhydrous magnesium sulfate, and concentrated under vacuum. The residue was purified by a silica gel column (Wako gel, C-300, 80 g, hexane:ethyl acetate=10:1, containing 2% Et$_3$N) to obtain 1.006 g (99%) of the compound (1c).

The compound (1c) 1.0 g (0.88 m mol) was dissolved in a mixed solution of dichloroethane 20 ml and methanol 1 ml, and TsOH (p-toluensulfonic acid monohydrate) 67 mg (0.35 m mol) was added to the reaction mixture followed by stirring at room temperature for 1 hour. A saturated aqueous solution of NaHCO$_3$ was added to the obtained reaction solution to neutralize the solution. After adding chloroform to the solution, the obtained chloroform solution was washed with water and a saturated aqueous solution of sodium chloride, dried over anhydrous magnesium sulfate, and subjected to vacuum distillation. The residue was purified by a silica gel column (Wako gel, C-300, 25 g, hexane:ethyl acetate=5:1) to obtain the compound (IX) 650 mg (83%).

Physical properties of the compound (IX)
Rf=0.113 (hexane:ethyl acetate=5:1)
[α]$_D^{25}$ 13.79 (C=0.425, EtOAc)
400 MHz NMR CDCl$_3$, TMS, ppm 0.879, 6H, t, J=6.5, —CH$_2\underline{CH_3}$×2, 1.066, 9H, s, t-butyl, 1.252, 62H, s, —CH$_2$—, 1.574, 2H, m, H-3', 1.869, 2H, m, H-6, 1.962, 2H, m, H-2', 3.621, 1H, d, d, d, J=2.9, 7.2, 11.0, H-1, 3.831, 1H, m, H-2, 3.887, 1H, d, d, d, J=2.6, 4.4, 11.1, H-1, 4.335, 1H, t, J=3.6, H-3, 5.370, 1H, dd, J=15.2, 5.5, H-4, 5.406, 1H, dt, J=15.2, 5.6, H-5, 7.34–7.66, 10H, m, aromatic protons

Example 8

The compound (IX) 100 mg (0.113 m mol) was dissolved in THF 2 ml and AgOTf 505 mg (1.96 m mol) dissolved in THF 1 ml were added to activated molecular sieves 4A 1 g followed by stirring for 10 minutes. The compound (V) 202 mg (0.34 m mol) dissolved in THF 1 ml was added slowly to the obtained reaction mixture at −20° C. followed by agitation at room temperature for 18 hours. The reaction mixture was filtered by using celite, the filtrate was diluted with EtOAc, washed with a saturate aqueous solution of sodium hydrogencarbonate, water and a saturate aqueous solution of sodium chloride, dried with anhydrous MgSO$_4$, and subjected to vacuum distillation. vacuum The residue was purified by a silica gel column (Wako gel, C-300, 25 g, toluene:EtOAc=1:1) to obtain the compounds (VII) (28.5 mg, 18.6%) and (VIII) (36.4 mg, 23.8%).

Physical properties of the compound (VII) Rf=0.46 (toluene:EtOAc=1:1) Elementary analysis: Calculated: C, 68.79; H, 9.47; N, 2.06; Found: C, 68.20; H, 9.34; N, 2.05.

NMR 400 MHz ppm CDCl$_3$ TMS, 0.879 (6H, s, CH$_3$33 2, J=7.0), 1.045 (9H, s, t-Bu), 1.919, 2.003, 2.031, 2.094, 2.138 (s, Ac×5), 2.404 (1H, 3-Heq, dd, J=12.70, 7.82), 3.75 (3H, s, OCH₃), 5.05 (m, 1H, H-4), 7.3–7.7 (m, 10H, Ph)

Physical properties of the compound (VIII)
Rf=0.42 (toluene:EtOAc=1:1)
Elementary analysis: Calculated: C, 67.01; H, 9.52; N, 2.00 (+2H₂O). Found: C, 66.95; H, 9.14; N, 2.18.
NMR 400 MHz ppm CDCl₃ TMS, 0.874 (6H, t, CH₃×2, J=7.0), 1.031 (9H, s, t-Bu), 1.884, 2.028, 2.041, 2.093, 2.128 (s, OAc×5), 2.532 (1H, dd, J=12.82, 4.76, H-3eq), 3.728 (3H, s, OCH₃) 4.858 (1H, m, H-4), 7.3–7.7 (10H, m, Ph).

What is claimed is:

1. A compound expressed by the following formula (1):

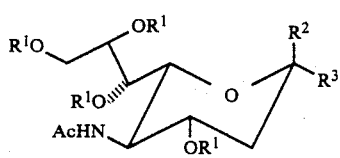

wherein R¹ denotes a hydrogen atom or CH₃CO—, R² denotes —COOR⁴ (R⁴ denotes Na or a methyl group) or

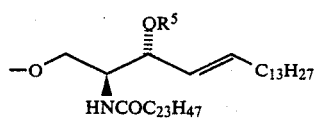

(R⁵ denotes a hydrogen atom, —COC₆H₅ or —Si(C₆H₅)₂C(CH₃)₃) and R³ denotes

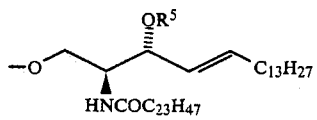

(R⁵ denotes a hydrogen atom, —COC₆H₅ or —Si(C₆H₅)₂C(CH₃)₃) when R² is —COOR⁴ (R⁴ denotes Na or a methyl group) or denotes —COOR⁴ when R² is

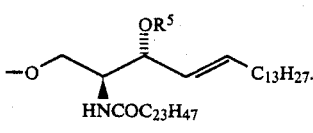

2. The compound of claim 1 wherein R¹ is CH₃CO—, R² is

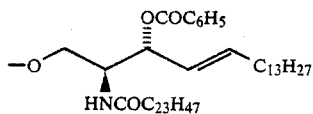

and R³ is —COOCH₃.

3. The compound of claim 1 wherein R¹ is CH₃CO—, R² is —COOCH₃ and R³ is

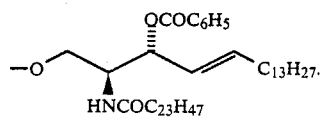

4. The compound of claim 1 wherein R¹ is a hydrogen atom, R² is

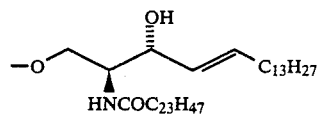

and R³ is —COONa.

5. The compound of claim 1 wherein R¹ is a hydrogen atom, R² is —COONa and R³ is

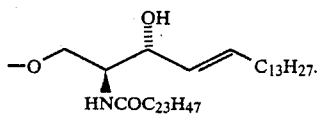

6. The compound of claim 1 wherein R¹ is CH₃CO—, R² is

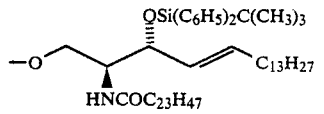

and R³ is —COOCH₃.

7. The compound of claim 1 wherein R¹ is CH₃CO—, R² is —COOCH₃ and R³ is

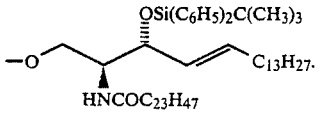

8. A method for producing sialosylceramides comprising the steps of
(i) reacting a compound (V) expressed by the following formula (1):

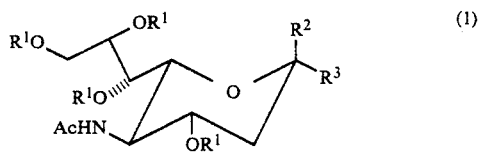

(wherein R¹ denotes an acetyl group, R² denotes a chlorine atom, and R³ denotes —CO₂CH₃) with

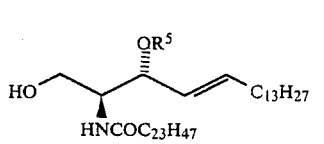

(R³ denotes —COC₆H₅ or —Si(C₆H₅)₂C(CH₃)₃ to form a compound (I) expressed by the formula (1) and a compound (II) shown by the formula (1); and (ii) deacetylating and debenzoylating or desilylating said compound (I) or (II) to form a compound (III) expressed by the formula (1) (wherein $R^1$ denotes a hydrogen atom, $R^2$ denotes

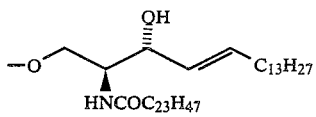

and $R^3$ denotes $—CO_2Na$) or a compound (IV) expressed by the formula (1) (wherein $R^1$ denotes a hydrogen atom, $R^2$ denotes $—CO_2Na$, and $R^3$ denotes

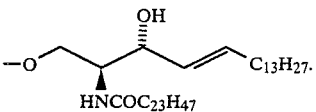

9. A method for producing sialosylceramides of claim 8 wherein the reaction of the compound (V) and

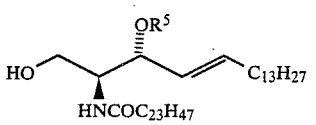

is carried out in the presence of molecular sieves 4A or AW300.

10. A method for producing sialosylceramides of claim 8 wherein the reaction of the compound (V) and

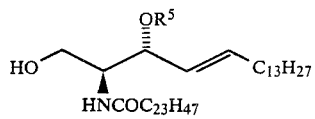

is carried out in the presence of a glycosidation catalyst.

11. A method for producing sialosylceramides of claim 10 wherein the glycosidation catalyst is silver triflate.

12. A method for producing sialosylceramides of claim 8 wherein the reaction of the compound (V) and

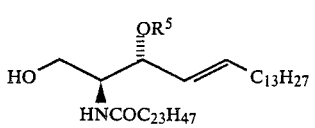

is carried out in the presence of a solvent.

13. A method for producing sialosylceramides of claim 12 wherein the solvent is dichloroethane, tetrahydrofuran, chloroform, nitromethane, a mixed solution of tetrahydrofuran and chloroform.

14. A method for producing sialosylceramides of claim 8 wherein the deacetylation and debenzoylation or desilylation of the compound (I) or (II) are conducted by reacting sodium methoxide with the compound (I) or (II) in methanol.

* * * * *